United States Patent
Sachs

(10) Patent No.: US 8,606,358 B2
(45) Date of Patent: *Dec. 10, 2013

(54) MUSCLE STIMULATOR

(71) Applicant: Mainstay Medical Limited, Swords (IE)

(72) Inventor: Dan Sachs, Minneapolis, MN (US)

(73) Assignee: Mainstay Medical Limited, Swords, County Dublin (IE)

(*) Notice: Subject to any disclaimer, the term of this patent is extended or adjusted under 35 U.S.C. 154(b) by 0 days.

This patent is subject to a terminal disclaimer.

(21) Appl. No.: 13/858,809

(22) Filed: Apr. 8, 2013

(65) Prior Publication Data

US 2013/0218247 A1    Aug. 22, 2013

Related U.S. Application Data

(63) Continuation of application No. 12/075,174, filed on Mar. 10, 2008, now Pat. No. 8,428,728.

(60) Provisional application No. 60/905,979, filed on Mar. 9, 2007.

(51) Int. Cl.
*A61N 1/18* (2006.01)

(52) U.S. Cl.
USPC ............................................. 607/43; 607/48

(58) Field of Classification Search
USPC .................... 607/2, 43, 46, 48, 117
See application file for complete search history.

(56) References Cited

U.S. PATENT DOCUMENTS

| | | | |
|---|---|---|---|
| 3,077,884 A | 2/1963 | Bartow et al. |
| 3,893,463 A | 7/1975 | Williams |
| 4,026,301 A | 5/1977 | Friedman et al. |
| 4,342,317 A | 8/1982 | Axelgaard |
| 4,408,609 A | 10/1983 | Axelgaard |
| 4,658,835 A | 4/1987 | Pohndorf |
| 5,501,452 A | 3/1996 | Halvorson |
| 5,522,854 A | 6/1996 | Ideker et al. |
| 5,916,172 A | 6/1999 | Hodges et al. |
| 6,104,957 A | 8/2000 | Alo et al. |
| 6,319,241 B1 | 11/2001 | King et al. |
| 6,406,421 B1 | 6/2002 | Grandjean et al. |
| 6,516,227 B1 | 2/2003 | Meadows et al. |

(Continued)

FOREIGN PATENT DOCUMENTS

| WO | WO-2006/133445 A2 | 12/2006 |
|---|---|---|
| WO | WO-2009/134475 A1 | 11/2009 |

OTHER PUBLICATIONS

Airaksinen et al., Chapter 4. European guidelines for the management of chronic nonspecific low back pain,European spine journal [I: official publication of the European Spine Society, the European Spinal DeformitySociety, and the European Section of the Cervical Spine Research Society 15 Suppl 2 (2006):S192-300. http://www.ncbi.nlm.nih.gov/pubmed/16550448.

(Continued)

*Primary Examiner* — Allen Porter, Jr.
(74) *Attorney, Agent, or Firm* — Foley & Lardner LLP; Nicola A. Pisano; Christopher C. Bolten

(57) ABSTRACT

An implantable medical device for treating the back of a patient. Stimulation energy is delivered to muscles or joint capsules or ligaments or nerve fibers to improve the heath of the back.

18 Claims, 5 Drawing Sheets

A. THORAROLUMBAR FASCIA
B. TRANSVERSE ABDOMINIS
C. ERECTOR SPINEE
D. PSOAS MAJOR
E. QUADRATUS LUMBORUM

(56) References Cited

U.S. PATENT DOCUMENTS

| | | |
|---|---|---|
| 6,671,557 B1 | 12/2003 | Gliner |
| 6,839,594 B2 | 1/2005 | Cohen et al. |
| 7,206,641 B2 | 4/2007 | Ignagni et al. |
| 7,239,918 B2 | 7/2007 | Strother et al. |
| 7,286,879 B2 | 10/2007 | Wallace |
| 7,317,948 B1 | 1/2008 | King et al. |
| 7,324,852 B2 | 1/2008 | Barolat et al. |
| 7,324,853 B2 | 1/2008 | Ayal et al. |
| 7,337,005 B2 | 2/2008 | Kim et al. |
| 7,337,006 B2 | 2/2008 | Kim et al. |
| 7,444,181 B2 | 10/2008 | Shi et al. |
| 7,447,546 B2 | 11/2008 | Kim et al. |
| 7,450,993 B2 | 11/2008 | Kim et al. |
| 7,489,561 B2 | 2/2009 | Armstrong et al. |
| 7,502,651 B2 | 3/2009 | Kim et al. |
| 7,580,753 B2 | 8/2009 | Kim et al. |
| 7,668,598 B2 | 2/2010 | Herregraven et al. |
| 7,684,866 B2 | 3/2010 | Fowler et al. |
| 7,930,039 B2 | 4/2011 | Olson |
| 8,082,039 B2 | 12/2011 | Kim et al. |
| 8,170,690 B2 | 5/2012 | Morgan et al. |
| 8,229,565 B2 | 7/2012 | Kim et al. |
| 8,229,656 B2 | 7/2012 | Ikushima et al. |
| 8,249,701 B2 | 8/2012 | Imran et al. |
| 8,380,318 B2 | 2/2013 | Kishawi et al. |
| 2001/0053885 A1 | 12/2001 | Gielen et al. |
| 2004/0111118 A1 | 6/2004 | Hill et al. |
| 2004/0236383 A1 | 11/2004 | Yelizarov |
| 2006/0111746 A1 | 5/2006 | Foreman et al. |
| 2006/0111754 A1 | 5/2006 | Rezai et al. |
| 2007/0027501 A1 | 2/2007 | Jensen et al. |
| 2007/0073357 A1 | 3/2007 | Rooney et al. |
| 2007/0100377 A1 | 5/2007 | Armstrong et al. |
| 2007/0100391 A1 | 5/2007 | Armstrong |
| 2009/0210041 A1 | 8/2009 | Kim et al. |
| 2010/0036454 A1 | 2/2010 | Bennett et al. |
| 2011/0224665 A1 | 9/2011 | Crosby et al. |
| 2011/0224682 A1 | 9/2011 | Westlund et al. |
| 2012/0035953 A1 | 2/2012 | Armstrong |
| 2012/0116477 A1* | 5/2012 | Crowe et al. ............ 607/46 |

OTHER PUBLICATIONS

Baker et al., "Clinical Uses of Neuromuscular Electrical Stimulation," NeuroMuscular Electrical Stimulation—A Practical Guide, 4th ed. Rancho Los Amimgos Research and Education Institute Inc., pp. 47-66 (2000).

Bhadra et al., "Peripheral nerve stimulation for restoration of motor function," Journal of Clinical Neurophysiology: Official Publication of the American Electroencephalographic Society, 14(5):378-33, Sep. 1997.

Bogie et al., "Effects of regular use of neuromuscular electrical stimulation on tissue health," Journal of Rehabilitation Research and Development, 40(6):469-475 (2003) available at: http://www.ncbi.nlm.nih.gov/pubmed/15077659 (Accessed Jan. 18, 2011).

Bowman et al., "Effects of Waveform Parameters on Comfort during Transcutaneous Neuromuscular Electrical Stimulation," Annals of Biomedical Engineering, 13:59-74 (1985).

Bradford et al., "Surface Electrical Stimulation in the Treatment of Idiopathic Scoliosis: Preliminary Results in 30 Patients," Spine, 8(7):757-764 (1983).

Brazier et al., "A Comparison of the EQ-5D and SF-6D Across Seven Patient Groups," Health Economics, 13:873-884 (2004).

Coghlan et al., "Electrical muscle stimulation for deep stabilizing muscles in abdominal wall," Conference proceedings: . . . Annual International Conference of the IEEE Engineering in Medicine and Biology Society. IEEE Engineering in Medicine and Biology Society. Conference, pp. 2756-2759 (2008) available at: http://www.ncbi.nlm.nih.gov/pubmed/19163276.

Coghlan et al., "Neuromuscular electrical stimulation training results in enhanced activation of spinal stabilizing muscles during spinal loading and improvements in pain ratings," Conference proceedings: . . . Annual International Conference of the IEEE Engineering in Medicine and Biology Society. IEEE Engineering in Medicine and Biology Society. Conference, pp. 7622-7625 (2011) available at: http://www.ncbi.nlm.nih.gov/pubmed/22256103.

Crago et al., "The choice of pulse duration for chronic electrical stimulation via surface, nerve, and intramuscular electrodes," Annals of Biomedical Engineering, 2(3):252-264 (1974).

Criterion Inc., "NMES Treatment Protocols," 3 pages (accessed Jun. 7,2012) available at http://www.criterionmed.com/PDF/NMES%20Treatment%20Protocols.pdf.

Durham et al., "Surface Electrical Stimulation Versus Brace in Treatment of Idiopathic Scoliosis," Spine, 15(9):888-891 (1990).

Empi, "Low Back Syndrome/Chronic Low Back Pain," NMES Guidelines for Treatment, 2 pages (2003).

Extended European Search Report dated Jan. 7, 2013 in related European Patent Appliction No. 12176863.

Ferreira et al., "Comparison of general exercise, motor control exercise and spinal manipulative therapy for chronic low back pain: A randomized trial," Pain, 131(1-2):31-37 (2007) available at: http://www.ncbi.nlm.nih.gov/pubmed/17250965.

Friedman et al., "Electrical stimulation for scoliosis," American Family Physician, 25(4):155-160 (1982) available at: http://www.ncbi.nlm.nih.gov/pubmed/6978055 (Accessed Oct. 19, 2011).

Garmirian et al., "Disciriminating Neurogenic from Myopathic Disease via Measurement of Muscle Anisotrophy," Muscle Nerve, 39(1):16-24 (2009) (abstract).

Glaser et al., "Electrical Muscle Stimulation as an Adjunct to Exercise Therapy in the Treatment of Nonacute Low Back Pain: A Randomized Trial," The Journal of Pain, 2(5):295-300 (2001).

Gorman et al., "The effect of stimulus parameters on the recruitment characteristics of direct nerve stimulation," IEEE Transactions on Bio-medical Engineering, 30(7):407-414 (1983).

Hagg et al., "The Clinical Importance of Changes in Outcome Scores After Treatment for Chronic Low Back Pain," Eur. Spine. J., 12:12-20 (2003).

Herbert et al., "Scoliosis Treatment in Children Using a Programmable, Totally Implantable Muscle Stimulator (ESI)," IEEE Transactions on Biomedical Engineering, 36(7):801 (Jul. 1989).

Hodges et al., "Intervertebral Stiffness of the Spine is Increased by Evoked Contraction of Transversus Abdominis and the Diaphragm: in Vivo Porcine Studies," Spine 28(23):2594-2601 (Dec. 1, 2003) (abstract).

Hodges et al., "Response of the deep paraspinal muscles to cortical but not transmastoid stimulation is increased at a single lumbar level following interverebral disc lesion," Progress in Motor Control Vi—Brazil. 36:2-3 (2007).

Hodges, "Is There a Role for Transversus Abdominis in Lumbo-Pelvis Stability?" Manual Therapy, 4(2):74-86 (1999).

Holm et al., "Sensorimotor Control of the Spine," J. Electromyogr. Kinesiol., 12(3):219-34 (Jun. 2002) (abstract).

Hortobagyi et al., "Neural adaptations to electrical stimulation strength training," European Journal of Applied Physiology, 2439-2449 (2011) available at: http://www.ncbi.nlm.nih.gov/pubmed/21643920 (Accessed Jul. 19, 2011).

International Search Report for PCT/US08/03126, 1 page, mailed Jun. 25, 2008.

Keller et al., "Muscular Contributions to Dynamic Dorsoventral Lumber Spine Stiffness," Eur. Spine J., 16(2):245-254 (Apr. 29, 2006).

Kiesel et al., "Measurement of lumbar multifidus muscle contraction with rehabilitative ultrasound imaging," Manual Therapy, 12(2):161-166 (2007) available at: http://www.ncbi.nlm.nih.gov/pubmed/16973400.

Lauridsen et al., "Responsiveness and Minimal Clinically Important Difference for Pain and Disability Instruments in Low Back Pain Patients," BMC Musculoskeletal Disorders, 7(82):16 pages (2006).

Miyatani et al., "Validity of Estimating Limb Muscle Volume By Bioelectrical Impedance," J. Appl. Physiol., 91:386-394 (2001).

Mortimer et al., "Intramuscular electrical stimulation: tissue damage," Annals of Biomedical Engineering, 8(3):235-244 (1980).

Mortimer et al., "Peripheral Nerve and Muscle Stimulation. In: Horch KW, Dhillon G, eds," Neuroprosthetics: Theory and Practice

(56) References Cited

OTHER PUBLICATIONS (Series on Bioengineering & Biomedical Engineering—vol. (2), World Scientific Publishing Company, pp. 1-48 (2005).
Nachemson et al., "Effectiveness of Treatment with a Brace in Girls Who Have Adolescent Idiopathic Scoliosis," The Journal of Bone and Joint Surgery, 77-A(6):815-819 (Jun. 1995).
Oaao Bock, "ActiGait Implantable Drop Foot Stimulator," Surgeon Manual, 28 pages (2006).
O'Donnell et al., "Electrical Stimulation in the Treatment of Idiopathic Scoliosis," Clinical Orthopaedics and Related Research, No. 229:107-112 (Apr. 1988).
Paicius et al., "Peripheral Nerve Field Stimulation for the Treatment of Chronic Low Back Pain: Preliminary Results of Long-Term Follow-up: A Case Series," Neuromodulation, 10(3):279-290 (2007) available at: http://www.blackwell-synergy.com/doi/abs/10.1111/j.1525-1403.2007.00116.x.
Panjabi, Manohar, "A hypothesis of chronic back pain: ligament subfailure injuries lead to muscle control dysfunction," European spine journal: official publication of the European Spine Society, the European Spinal Deformity Society, and the European Section of the Cervical Spine Research Society 15, No. 5 (May 2006): 668-676. http://www.ncbi.nlm.nih.gov/pubmed/16047209.
Panjabi, Manohar, "The stabilizing system of the spine. Part 1. Function, dysfunction, adaptation, and enhancement," Journal of Spinal Disorders, 5(4)383-389 (Dec. 1992), Discussion 397. http://www.ncbi.nlm.nih.gov/pubmed/1490034.
Panjabi, Manohar, "The stabilizing system of the spine. Part II. Neutral zone and instability hypothesis," Journal of Spinal Disorders, 5(4):390-396 (Dec. 1992), Discussion 397. http://www.ncbi.nlm.nih.gov/pubmed/1490035.
Peckham et al., "Functional electrical stimulation for neuromuscular applications," Annual review of Biomedical Engineering, 7:327-360 (2005) available at: http://www.ncbi.nlm.nih.gov/pubmed/16004574.
Peterson et al., "Long-term intramuscular electrical activation of the phrenic nerve: safety and reliability," IEEE Transactions on Biomedical Engineering, 41(12):1115-1126 (1994).
Poitras et al., "Evidence-informed management of chronic low back pain with transcutaneous electrical nerve stimulation, interferential current, electrical muscle stimulation, ultrasound, and thermotherapy," The Spine Journal 8:226-233 (2008).
Reed B., :The Physiology of Neuromuscular Electrical Stimulation, Pediatric Physical Therapy, 9(3):96-102 (1997) available at: http://journals.lww.com/pedpt/pages/articleviewer.aspx?year=1997&issue=00930&article=00002&type=abstract.
RS Medical, "RS-4M Muscle Stimulator," available at http://www.rsmedical.com/documents/fact_sheet_RS4m.pdf (last visited Jul. 19, 2012).

Rutkove, "Electrical Impedance Myography: Background, Current State, and Future Directions," Muscle Nerve, 40(6):936-946 (2009).
Schwartz et al., "Therapeutic Electrical Stimulation of the Hypoglossal Nerve in Obstructive Sleep Apnea," Arch Otolaryngal Head Neck Surg., 127:1216-1223 (2001).
Sheffler et al., "Neuromuscular Electrical Stimulation in Neurorehabilitation," Muscle Nerve, 35: 562-590 (2007).
Solomonow et al., "The Ligamento-Muscular Stabilizing System of the Spine," Spine, 23(23):2552-2562 (1998).
Spinal Fusion Guidelines, MD Guidelines, 2009. www.mdguidelines.com/spinal-fusion.
Stokes et al., "Surface EMG Electrodes Do Not Accurately Record from Lumbar Multifidus Muscles," Clin. Biomech., 18(1):9-13 (2003) (abstract).
Van Dieen et al., "Trunk Muscle Recruitment Patterns," Spine, 28(8):834-841 (2003) (abstract).
Van et al., "The use of real-time ultrasound imaging for biofeedback of lumbar multifidus muscle contraction in healthy subjects," The Journal of Orthopaedic and Sports Physical Therapy, 36(12):920-925 (2006) available at: http://www.ncbi.nlm.nih.gov/pubmed/17193869.
Van Zundert et al., "Radiofrequency treatment for chronic pain syndromes," CPD Anaesthesis, 6(1):13-17 (2004).
Verrills et al., "Peripheral Nerve Stimulation: A Treatment for Chronic Low Back Pain and Failed Back Surgery Syndrome?," Neuromodulation: Technology at the Neural Interface, 12(1):68-75 (2009).
Vrbova et al., Application of Muscle/Nerve Stimulation in Health and Disease, Springer Verlag (2008) available at: http://books.google.com/books?hl=en&lr=&id=jb8fDGxkbgEC&oi=fnd&pg=PAI&dq=Application of Muscle/Nerve Stimulation in Health and Disease&ots=CMV5rXiDQD&sig=Wg8u1YOC4PgvVDzcjdwBub5U2To (Accessed Jun. 2, 2011).
Wallwork et al., "The effect of chronic low back pain on size and contraction of the lumbar multifidus muscle," Manual Therapy, 14(5):496-500 (2009) available at: http://www.ncbi.nlm.nih.gov/pubmed/19027343.
Ward et al., "Architectural analysis and intraoperative measurements demonstrate the unique design of the multifidus for lumbar spine stability," J. Bone Joint Surg. [Am.] 91:176-185, PMC2663324 (2009).
Wright et al., "Morphologic and histochemical characteristics of skeletal muscle after long-term intramuscular electrical stimulation," Spine, 17(7):767-770 (1992) available at: http://www.ncbi.nlm.nih.gov/pubmed/1502640 (Accessed Aug. 2, 2011).
Written Opinion for PCT/US08/03126, 7 pages, mailed Jun. 25, 2008.

* cited by examiner

A. THORAROLUMBAR FASCIA
B. TRANSVERSE ABDOMINIS
C. ERECTOR SPINEE
D. PSOAS MAJOR
E. QUADRATUS LUMBORUM

F. ANTERIOR LONGITUDINAL LIGAMENT
G. POSTERIOR LONGITUDINAL LIGAMENT
H. LIGAMENTUM FLAVUM
J. SUPRASPINOUS LIGAMENT
K. INTERSPINOUS LIGAMENT
L. SACROILIAC LIGAMENT

MUSCLE STIMULATOR

CROSS REFERENCE TO RELATED CASES

This application is a continuation of U.S. patent application Ser. No. 12/075,174, filed Mar. 10, 2008, now U.S. Pat. No. 8,428,728, which claims the benefit of U.S. Provisional Application No. 60/905,979, filed Mar. 9, 2007, the entire contents of all of which are incorporated herein by reference.

FIELD OF THE INVENTION

The present invention relates to medical devices and more particularly to a stimulator for treating muscles and neural pathways in the back.

BACKGROUND OF THE INVENTION

The human back is a complicated structure including bones, muscles, ligaments, tendons, nerves and other structures. The spinal column consists of interleaved vertebral bodies and intervertebral discs. These joints are capable of motion in several planes including flexion-extension, lateral bending, axial rotation, longitudinal axial distraction-compression, anterior-posterior sagittal translation, and left-right horizontal translation. The spine provides connection points for a complex collection of muscles that are subject to both voluntary and involuntary control.

Back pain is common and recurrent back pain in the lower or lumbar region of the back is well documented. The exact cause of most back pain remains unproven. One common notion is that some cases of back pain are caused by abnormal mechanics of the spinal column. Degenerative changes, injury of the ligaments, acute trauma, or repetitive microtrauma may lead to back pain via inflammation, biochemical and nutritional changes, immunological factors, changes in the structure or material of the endplates or discs, and pathology of neural structures.

The spinal stabilization system was conceptualized by Manohar Panjabi to consist of three subsystems: 1) the spinal column, to provide intrinsic mechanical stability; 2) spinal muscles surrounding the spinal column to provide dynamic stability; and 3) the neuromotor control unit to evaluate and determine requirements for stability via a coordinated muscle response. In patients with a functional stabilization system, the three subsystems work together to provide mechanical stability.

The spinal column consists of vertebrae and ligaments (e.g. spinal ligaments, disc annulus, and facet capsules). There is an abundance of in-vitro work in explanted cadaver spines and models evaluating the relative contribution of various spinal column structures to stability, and how compromise of a specific column structure will lead to changes in the range of motion of spinal motion segments.

The spinal column also has a transducer function, to generate signals describing spinal posture, motions, and loads via mechanoreceptors present in the ligaments, facet capsules, disc annulus, and other connective tissues. These mechanoreceptors provide information to the neuromuscular control unit, which generates muscle response patterns to activate and coordinate the spinal muscles to provide muscle mechanical stability. Ligament injury, fatigue, and viscoelastic creep may corrupt signal transduction. If spinal column structure is compromised, due to injury, degeneration, or viscoelastic creep, then muscular stability is increased to compensate and maintain stability.

Muscles provide mechanical stability to the spinal column. This is apparent by viewing cross section images of the spine, as the total area of the cross sections of the muscles surrounding the spinal column is much bigger than the spinal column itself. Additionally, the muscles have much larger lever arms than those of the intervertebral disc and ligaments Under normal circumstances, the mechanoreceptors generate signals to the neuromuscular control unit for interpretation and action. The neuromuscular control unit produces a muscle response pattern based upon several factors, including the need for spinal stability, postural control, balance, and stress reduction on various spinal components.

It is believed that in some patients with back pain, the spinal stabilization system is dysfunctional. With soft tissue injury, mechanoreceptors may produce corrupted signals about vertebral position, motion, or loads, leading to an inappropriate muscle response. In addition, muscles themselves may be injured, fatigued, atrophied, or lose their strength, thus aggravating dysfunction of the spinal stabilization system. Conversely, muscles can disrupt the spinal stabilization system by going into spasm, contracting when they should remain silent, or contracting out of sequence with other muscles. As muscles participate in the feedback loop via mechanoreceptors in the form of muscle spindles and golgi tendon organs, muscle dysfunction could further compromise normal muscle activation patterns via the feedback loops.

Trunk muscles may be categorized into local and global muscles. The local muscle system includes deep muscles, and portions of some muscles that have their origin or insertion on the vertebrae. These local muscles control the stiffness and intervertebral relationship of the spinal segments. They provide an efficient mechanism to fine-tune the control of intervertebral motion. The lumbar multifidus, with its vertebra-to-vertebra attachments is an example of a muscle of the local system. Another example is the transverse abdominis, with its direct attachments to the lumbar vertebrae through the thoracolumbar fascia.

The multifidus is the largest and most medial of the lumbar back muscles. It consists of a repeating series of fascicles which stem from the laminae and spinous processes of the vertebrae, and exhibit a constant pattern of attachments caudally. These fascicles are arranged in five overlapping groups such that each of the five lumbar vertebrae gives rise to one of these groups. At each segmental level, a fascicle arises from the base and caudolateral edge of the spinous process, and several fascicles arise, by way of a common tendon, from the caudal tip of the spinous process. Although confluent with one another at their origin, the fascicles in each group diverge caudally to assume separate attachments to the mamillary processes, the iliac crest, and the sacrum. Some of the deep fibers of the fascicles which attach to the mamillary processes attach to the capsules of the facet joints next to the mamillary processes. All the fasicles arriving from the spinous process of a given vertebra are innervated by the medial branch of the dorsal ramus that issues from below that vertebra.

The global muscle system encompasses the large, superficial muscles of the trunk that cross multiple motion segments, and do not have direct attachment to the vertebrae. These muscles are the torque generators for spinal motion, and control spinal orientation, balance the external loads applied to the trunk, and transfer load from the thorax to the pelvis. Global muscles include the oblique internus abdominis, the obliquus externus abdmonimus, the rectus abdominus, the lateral fibers of the quadratus lumborum, and portions of the erector spinae.

Normally, load transmission is painless. Over time, dysfunction of the spinal stabilization system will lead to instability, resulting in overloading of structures when the spine moves beyond its neutral zone. The neutral zone is the range of intervertebral motion, measured from a neutral position, within which the spinal motion is produced with a minimal internal resistance. High loads can lead to inflammation, disc degeneration, facet joint degeneration, and muscle fatigue. Since the endplates and annulus have a rich nerve supply, it is believed that abnormally high loads may be a cause of pain. Load transmission to the facets may also change with degenerative disc disease, leading to facet arthritis and facet pain.

For patients believed to have back pain due to instability, clinicians offer treatments intended to reduce intervertebral motion. Common methods of attempting to improve muscle strength and control include core abdominal exercises, use of a stability ball, and Pilates. Spinal fusion is the standard surgical treatment for chronic back pain. Following fusion, motion is reduced across the vertebral motion segment. Dynamic stabilization implants are intended to reduce abnormal motion and load transmission of a spinal motion segment, without fusion. Categories of dynamic stabilizers include interspinous process devices, interspinous ligament devices, and pedicle screw based structures. Total disc replacement and artificial nucleus prostheses also aim to improve spine stability and load transmission while preserving motion.

There are a number of problems associated with current implants that aim to restore spine stabilization. First, it is difficult to achieve uniform load sharing during the entire range of motion if the location of the optimum instant axis of rotation is not close to that of the motion segment during the entire range of motion. Second, cyclic loading of dynamic stabilization implants may cause fatigue failure of the implant, or the implant-bone junction (e.g. screw loosening). Third, implantation of these systems requires surgery, which may cause new pain from adhesions, or neuroma formation. Moreover, surgery typically involves cutting or stripping ligaments, capsules, muscles, and nerve loops which will interfere with the spinal stabilization system.

SUMMARY OF THE INVENTION

It is the conjecture and surmise of the inventor that one source of pain results from mechanical instability of the back. Reaction to pain may in fact induce further instabilities within the back, setting up an overall decline in back health. It is the conjecture and surmise of the inventor that episodic electrical stimulation of particular groups of muscles and associated nerves, ligaments, or joint capsules within the lower back can both reduce the severity of pain and reduce the frequency of pain exacerbations by enhancing stability of the mechanical structures of the lower back. The stimulation may serve to "train" the muscles and improve the tone, endurance, and strength of the muscles. The stimulation may also alter the stiffness of the back acutely during stimulation. The stimulation may also improve voluntary or involuntary motor control of muscles involved in spinal stabilization. The stimulation may also improve reflex arc activity between mechanoreceptors embedded within muscles, ligaments, or joint capsules, and the spinal cord, thereby enabling quick stabilization of the spinal column in the event of unexpected loads or movements. The stimulation may also be used to inhibit muscle spasticity and muscle spasm. Protocols have been developed for the use of muscle stimulation to accomplish each of these objectives to treat a variety of clinical disorders.

The device will be at least partially implanted and include a lead system that may be coupled to a boney structure within the back to provide stable placement of the lead. The lead or leads will likely be placed in muscle and the electrical stimulation will activate the nerves associated with the muscle. In another embodiment, the lead will directly stimulate target muscles which attach directly to the spinal column, without causing intentional activation of efferent nerve fibers. Target muscles for lead placement include muscles associated with local segmental control of a motion segment, including the deep multifidus, and transversus (or transverse) abdominis. Target muscles may also include muscles such as the diaphragm or pelvic floor muscles, that when stimulated, cause contraction of local segmental muscles.

The optimal location is not known. It is expected that some muscle fibers will be activated and that some nerve fibers will be activated. An induced contraction is expected to activate stretch receptors in the back. This may cause further muscle contractions via intact neural pathways. The result of a neuromuscular stimulus is expected to trigger a cascade of reactions.

In another embodiment, leads may be placed adjacent to receptors which, when stimulated, result in reflex contraction or increased tone of the local segmental control muscles. Target sites for stimulation include the disc annulus, facet capsule, interspinous ligament, supraspinous ligament, and sacro-iliac joint. Electrical stimulation may be used to activate monosynaptic stretch reflexes, which involve stretch of a muscle spindle generating an afferent impulse from the receptor region of the spindles to excite the alpha motoneurons in the same muscle, resulting in contraction. Electrical stimulation may be used to activate short-latency reflexes in the paraspinal muscles, which activate the paraspinal muscles en-masse. Electrical stimulation may be used to stimulate afferent fibers of distant musculoskeletal structures, such as the limbs, which may result in contraction of local segmental muscles in the spine. Electrical stimulation may be used to activate long-loop reflexes, which involve information processing at higher levels of the nervous system, including transcortical mechanisms.

Stimulation parameters for restoring muscle endurance, strength, or motor control are known in the field of physical medicine and rehabilitation, where electrical stimulation is used as a therapeutic tool to preserve or restore muscle function during immobilization, or in diseased, deinnervated, or atrophied muscle. It is anticipated that embodiments of our device may use stimulation parameters (e.g. pulse amplitude, frequency, width, duration, duty cycle, shape, ramp times, wave forms, voltage) that have been previously used in these other applications.

Electrical stimulation has been used to help patients improve their own voluntary control of apparently paralyzed muscles. For example, muscle stimulation has been used to improve motor control of limbs and swallowing function in patients following stroke or head injury. Facilitation is a term used to describe a treatment program aimed at enhancing volitional motor control for a patient who is experiencing dysfunction in the central nervous system. In patients recovering from central nervous system insult or partial denervation of muscle, the ability of the patient to "find" and contract the muscle is compromised. Neuromuscular facilitation implies the use of stimulation to augment voluntary efforts. One embodiment of a device for facilitation of spinal stabilization would use a sensor of multifidus activity (or activity of another muscle of the local muscle system) that would trigger a piggyback stimulation on top of a patient's native contraction. Stimulus amplitudes may be set to achieve a strong muscle contraction, or may be used simply as a sensory reminder. As the patient's motor control improves, stimulation amplitude may be decreased to provide only a sensory cue as to when the multifidus should contract.

Reeducation is a term used to describe a treatment program to enhance motor control for those patients who have altered voluntary recruitment of the muscular system due to some peripheral change, such as pain or disuse. Motor facilitation and reeducation are basically the same stimulation program, applied to a different patient population. Surgery, pain, trauma, disc herniation, or edema may make it difficult for a patient with an intact central nervous system to recruit a local stabilization muscle, such as the multifidus. This difficulty may be attributed to active inhibition of the motoneurons of the affected muscles through pain afferents. Inhibition, from whatever source, may lower the excitability of the motoneurons sufficiently to make them difficult to recruit. Electrical stimulation activates the large nerve fibers, preferentially. Thus stimulation near the nerve supply to the multifidus will recruit the large, Ia spindle afferents before visible muscle contraction is achieved. The effect of this Ia activation is to facilitate the motoneurons of the same motor pool, increasing excitability of the motor neuron pool through partial depolarization of the hyperpolarized, inhibited motoneurons. In addition, electrical stimulation can be used to supply sensory input about how a desired multifidus muscle contraction should feel, so that eventually a patient can do so voluntarily. It is anticipated that embodiments of our device may use stimulation parameters to improve motor control of spine stabilization muscles.

It is believed that some patients with back pain have inappropriately active global muscles, and that restoration of normal spine stabilization will require that these global muscles remain quiet, unless needed for the generation of torque. One embodiment of the invention involves use of stimulation parameters to inhibit contraction of global muscles through direct stimulation of the target muscle, or indirect stimulation via its motor nerve fiber. Another embodiment of the invention would stimulate antagonist muscles for the inhibition of agonist muscle contraction. This reciprocal inhibition is due to stimulation of the Ia afferents, which subsequently inhibit antagonist motoneurons. Another embodiment of the invention to inhibit abnormal contraction may rely on the phenomenon known as sensory habituation. Low amplitude stimulation given repeatedly has been reported to reduce muscle spasticity, given at either low frequency or high frequency. It is believed that the central nervous system allows repetitive information to be suppressed, and in the process, other related neural systems also come under inhibition. Stimulation is done at sensory levels only, for several hours at a time, on either the side of the muscle spasm, or the opposite side.

EMG sensing may be included in the implanted device to monitor and to modulate the degree of muscle activity of specific muscles of the back, and the training protocol for specific muscle groups. Other sensors may be used, such as pressure sensors, motion sensors, and nerve conduction sensors. The therapy can be titrated to obtain ideal support or control of the back to alleviate pain. The net result of the therapy is the restoration of muscle and motor control function to improve stability, and reduce the severity and recurrence of otherwise chronic or recurring back pain, or leg pain in the case of spinal stensosis. The device can be used as a standalone therapy or adjunctive to other procedures. In this context the inventor notes that disectomy and fusion operations, and procedures to insert medical device implants weaken, displace, and injure the muscles, ligaments, and nerves near the surgical site.

DETAILED DESCRIPTION

Figure 1A:
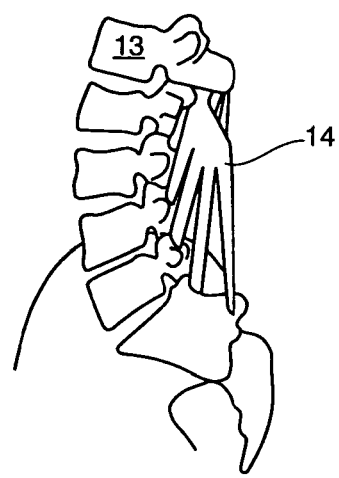
FIG. 1 is a schematic view of the muscle and nerve stimulation targets within the back of a patient. The figure is divided into three panels FIG. 1A, FIG. 1B and FIG. 1C.
Figure 1B:
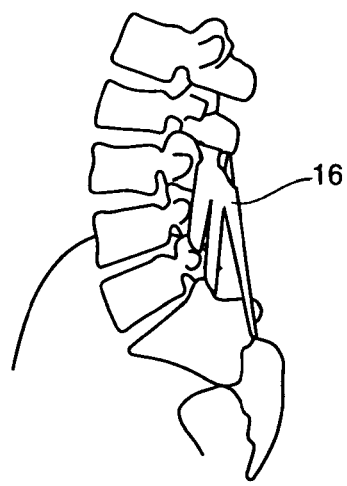
Figure 1C:
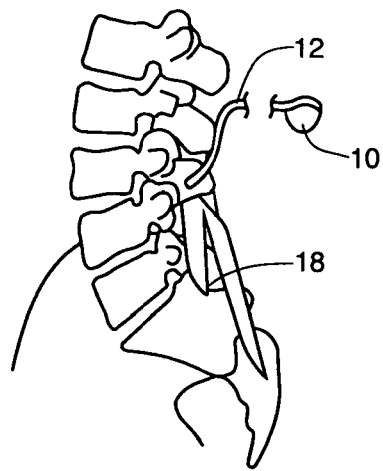

FIG. 1 shows a schematic representation of the back and in particular shows the connection of three sets of multifidus (MF) muscle fascicles labeled 14, 16 and 18 in panel of FIG. 1A, FIG. 1B and FIG. 1C respectively. In each panel the identified multifidus muscles are portrayed in a lateral view attached to a set of spinal vertebrae. Note that MF fascicles 14 arising from the spinous process and common tendon of L1 (the first lumbar vertebra) 13 insert into the mamillary processes of L4, L5, and S1, and the posterior superior iliac spine. Likewise MF fascicles 16 arising from the base of the spinous process and common tendon of L2 insert into the mamillary processes of L5 and S1, the posterior superior iliac spine, and the iliac crest. MF fascicles 18 arising from the base of the spinous process and common tendon of L3 insert into the mamillary process of the sacrum, and a narrow area extending caudally from the caudal extent of the posterior superior iliac spine to the lateral edge of the sacrum.

Although shown in isolation the MF fascicles overlap and cooperate to impose stability and strength to the back. It is recognized that the spinal stabilization system consist of three subsystems: 1) the spinal column consisting of sets of vertically stacked vertebral bodies typified by vertebrae and the associated ligaments and intervertebral discs (not shown), to provide intrinsic mechanical stability; 2) spinal muscles surrounding the spinal column to provide dynamic stability; and 3) the neuromotor control unit to evaluate and determine requirements for stability via a coordinated muscle response. In patients with a functional stabilization system, the three subsystems work together to provide mechanical stability. In panel FIG. 1C the implanted pulse generator 10 is shown near the lead system 12 that places electrodes (not shown) within the multifidus muscle structures.

Figure 3:
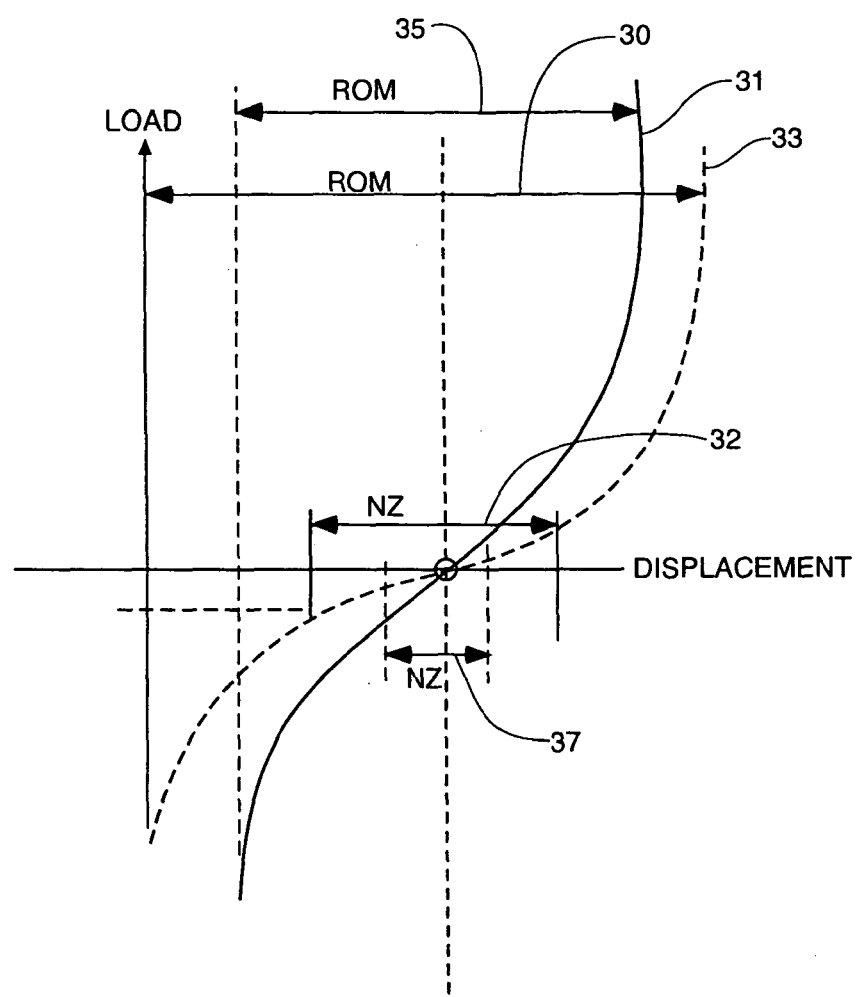
FIG. 3 is a graph depicting potential observable mechanical improvements to back function as a result of the therapeutic stimulation regime.

FIG. 3 is a graph displaying displacement as a function of load for a spine. The stability of a spinal motion segment may be measured and presented as seen in FIG. 3. With a load applied to the spinal column the normal motion segment exhibits a range of motion (ROM) 30. The response is non linear overall but at a neutral point a neutral zone (NZ) 32 of the response is approximately linear. The neutral zone is a region of laxity around the neutral resting position of a spinal motion segment, where little resistance is offered.

The applicant believes that the neutral zone is a parameter that correlates well with instability of the spinal system. It has been found to increase with back injury, muscle weakness, and degeneration. The goal of the therapy is to drive this measured load response to a narrower NZ by improving muscle function. The applicant surmises that the displacement of vertebrae can be detected correlating to normal and abnormal NZ using presently available motion tracking or position sensing devices that are well known in the art.

It is the goal of the therapy to stimulate these MF muscles to train them. This training should lead to a more normal NZ. For example, a pretreatment NZ 32 should improve to a more normal NZ 37 post treatment.

In FIG. 1C, a representative implementation of the invention may be carried out with a fully implanted pulse generator (IPG) 10 coupled to an implanted lead system 12. Together the IPG 10 and lead system 12 stimulate the MF muscle, as shown in the panels of the figure.

Figure 2:
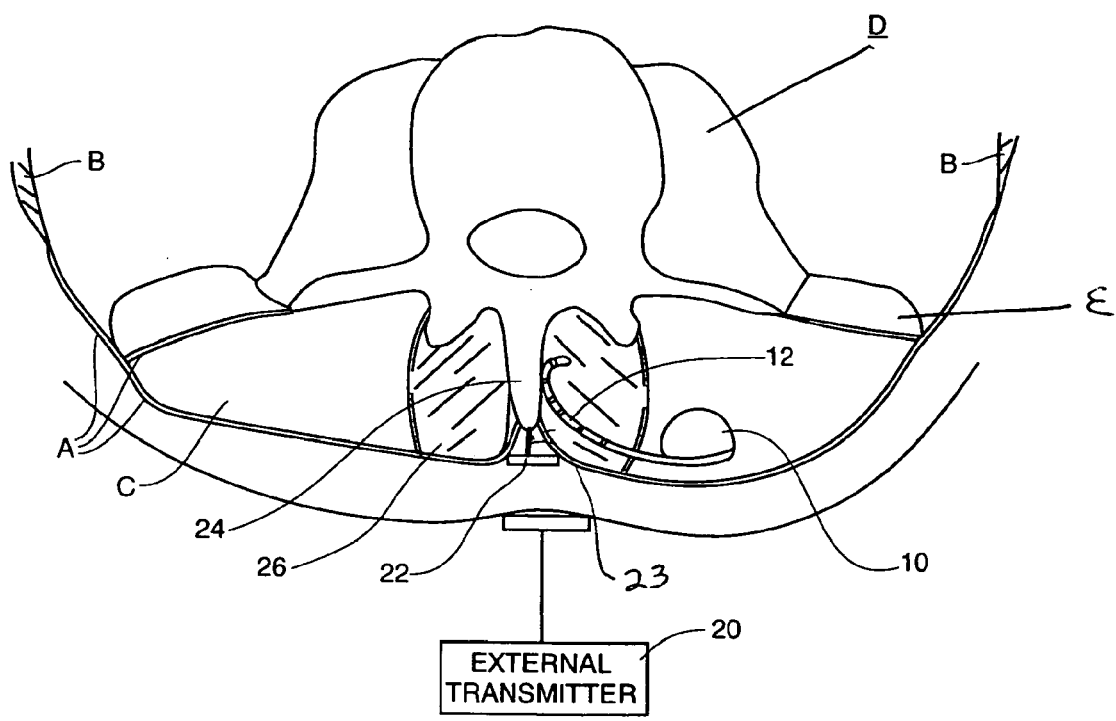
FIG. 2 is a schematic view of an exemplary implementation of a system to carry out the invention.

FIG. 2 shows a percutaneous lead placement with a lead system attached to a boney structure of a vertebra, more particularly on the spinous process 24 although the transverse process, the lamina or the vertebral body are candidate anchor points as well. It is expected that the transverse process will be the optimal location since the medial branch of the dorsal root of the spinal nerve courses over the transverse process. Although the primary targets of the stimulation are the deep fibers of lumbar multifidus 26, there are complicated mechanical and neural relations between this relatively large muscle group and companion groups. For this reason it is possible that additional candidate targets will include alone or in combinations other muscle groups including the quadratus lumborum, the erector spinae, psoas major, and transverse abdominis, or connective tissue such as the annulus or facet capsule that when stimulated will cause reflex contraction of a spinal muscle. In FIG. 2 a fully implanted IPG based system is shown with a pulse generator 10 coupled to an implanted lead system 12. As an alternative a hybrid system is shown. In the hybrid system an external transmitter 20 couples to an implanted receiver stimulator 22.

Although direct implantation of stimulation electrodes in muscle tissue is anticipated, the purpose of the stimulation is to depolarize innervated sections of the muscle that will then propagate a depolarization stimulus along the nerve fibers recruiting muscle tissue remote from the site of stimulation. Induced motions and tensions in muscle may activate stretch receptors and result in a cascade response of related muscle groups. Transvenous stimulation may be possible as well, however vessels of a suitable size for lead placement are not always found in desirable locations near the target stimulation site.

Stimulation electrodes may be used to modulate nerve activity, including inhibiting nerve conduction, improving nerve conduction, and improving muscle activity. It is expected that stimulation parameters will be developed experimentally with animal models and most likely human studies. The literature and clinical studies suggest that the energy levels for stimulation are well within the energy levels produced by modern pacing devices. The strength of the stimuli and duration of the stimulation are expected to improve the strength, endurance, or motor control of the muscles, thereby reducing instability of the back.

Figure 4:
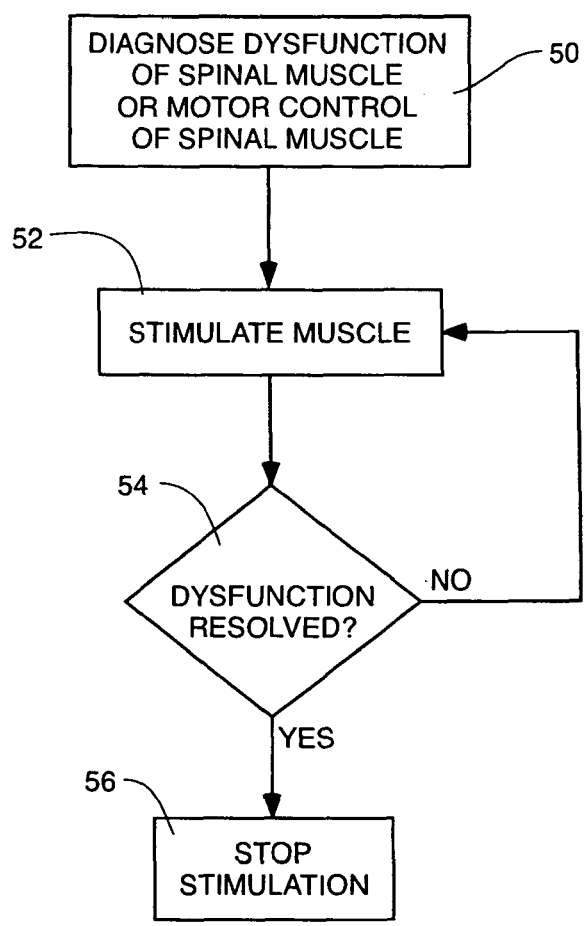
FIG. 4 is a flow chart representing a step wise method of carrying out an exemplary embodiment of the invention.

FIG. 4 shows a flowchart describing a process or method carried out with the implantable pulse generator. Modern programmable devices are well known and the flowchart is sufficient to enable one to carry out this embodiment of the invention. In step 50 the patient is diagnosed with a defect in the spinal muscle or motor control system. The patient may exhibit an inappropriate response as depicted by curve 33 in FIG. 3. At step 52 electrical stimulation is given to the muscle fascicles and related structures. The timing, magnitude and duration of the treatment will need to be titrated for the patient. In step 54 the patient is tested and if the dysfunction is resolved as indicated perhaps by MRI, ultrasound, EMG, physical examination, tissue biopsy or improved stability evidenced by curve 31 of FIG. 3 then the stimulation and train is stopped. Otherwise the treatment continues.

Figure 5:
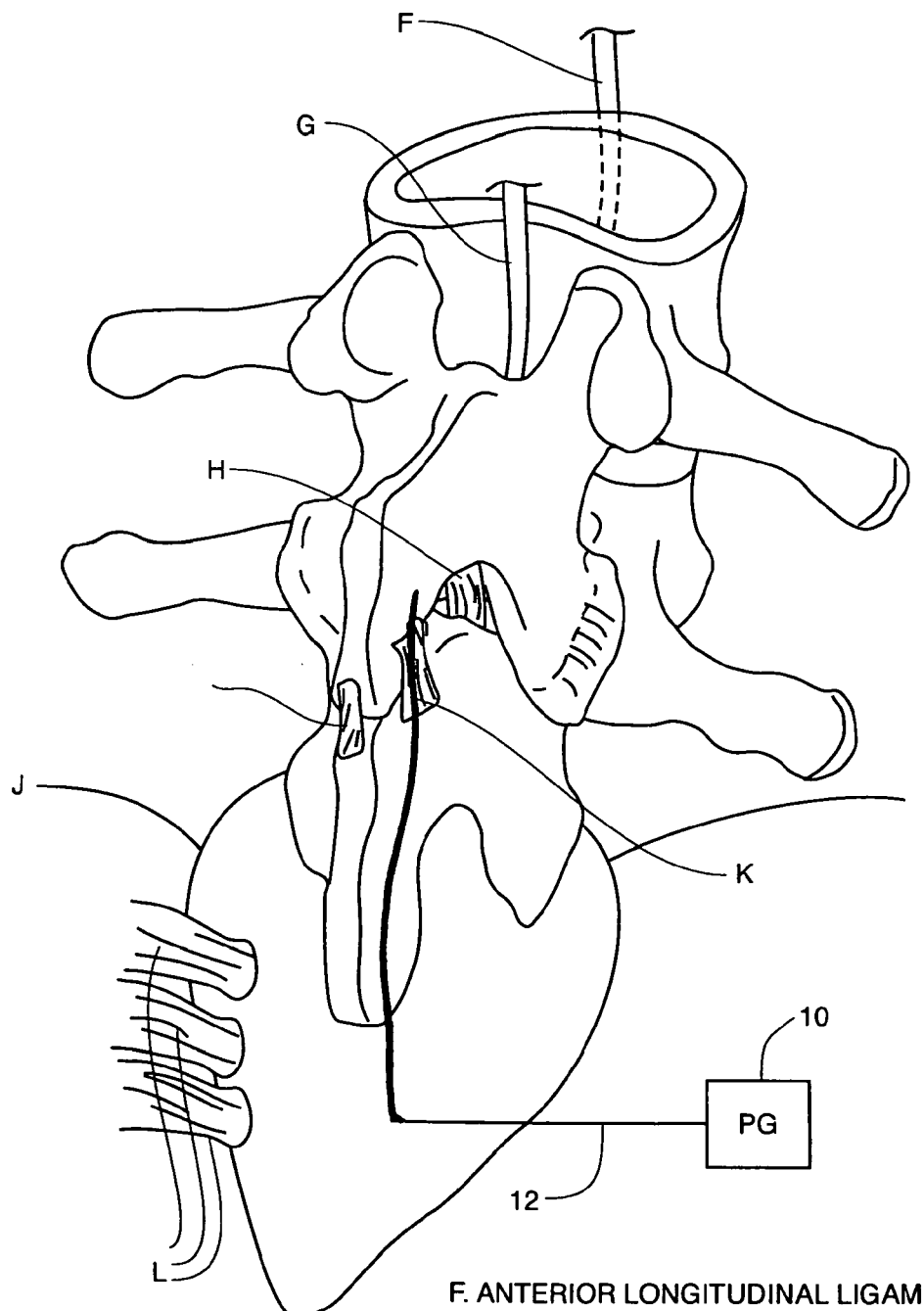
FIG. 5 is a schematic view of potential stimulation sites on ligaments, which may lead to increased tone of the spine stabilization muscles.

FIG. 5 shows the location of ligaments coupling bony structures of the spine. It is expected that electrical stimulation of these elements via lead system 12 will facilitate the therapy. As can be seen in the figure the ligaments lie close to the bone. The lead system 12 is placed along the bony structures and in an embodiment is anchored to the bone. Both active and passive fixation anchors are contemplated as well as glue based fixation features. Each of the ligaments and joint capsules enumerated in FIG. 5 are targets for stimulation.

DEFINITIONS

There is no well accepted metric for expressing all of the physical changes brought about by the therapeutic stimulation regime disclosed herein. For this reason the following terms are defined herein as follows:

Stiffness is a measure of resistance to displacement when a force is applied.

Strength is the force generating capacity of a muscle.

Endurance is resistance to fatigue.

Motor control is the ability of a patient to activate a muscle.

Muscle function refers to strength, endurance, or motor control. Improving one of these three variables, alone or in combination, can improve muscle function to accomplish a specific task.

It is desirable to provide real time therapy in an ambulatory patient. This is best achieved by a fully implantable system. Alternatively, a hybrid system with an implanted component communicating with an external stimulator may be best suited for intermittent use for example with supine patients at times of rest.

What is claimed is:

1. A method of modulating nervous tissue associated with a multifidus muscle to improve spinal stability, the method comprising:
    implanting an electrode in or adjacent to nervous tissue associated with the multifidus muscle; and
    providing electrical stimulation from the electrode to stimulate the nervous tissue associated with the multifidus muscle to rehabilitate function of the multifidus muscle and improve spinal stability.

2. The method of claim 1, wherein the nervous tissue comprises a dorsal ramus nerve.

3. The method of claim 1, wherein the nervous tissue comprises a medial branch of a dorsal ramus nerve.

4. The method of claim 1, wherein implanting the electrode comprises anchoring a fixation anchor, coupled to the electrode, to or alongside a boney structure.

5. The method of claim 1, wherein implanting the electrode comprises implanting a lead having the electrode such that the electrode is in or adjacent to the nervous tissue associated with the multifidus muscle.

6. The method of claim 5, wherein implanting the lead comprises anchoring a fixation anchor, coupled to the lead, to or alongside a boney structure.

7. The method of claim 5, wherein implanting the lead comprises anchoring a fixation anchor, coupled to the lead, to or alongside a boney structure of a spine selected from the group consisting of a spinous process, transverse process, lamina or vertebral body.

8. The method of claim 5, wherein the lead has one or more additional electrodes.

9. The method of claim 1, wherein providing electrical stimulation causes contraction of the multifidus muscle.

10. The method of claim 1, further comprising implanting a pulse generator coupled to the electrode.

11. The method of claim 10, wherein the pulse generator is internally powered.

12. The method of claim 10, wherein the pulse generator is coupled to a lead having the electrode.

13. The method of claim 1, wherein providing electrical stimulation comprises providing episodic electrical stimulation.

14. The method of claim 1, further comprising titrating at least one of timing, magnitude, and duration of the electrical stimulation for a patient.

15. The method of claim 1, further comprising diagnosing a defect in spinal muscle or motor control system.

16. The method of claim 1, further comprising testing function of the multifidus muscle.

17. The method of claim 16, wherein the testing comprises testing using at least one of MRI, ultrasound, EMG, physical examination, and tissue biopsy.

18. The method of claim 16, wherein the testing comprises testing displacement as a function of load for a spine.

* * * * *